United States Patent [19]

Bey et al.

[11] 4,374,128
[45] Feb. 15, 1983

[54] SUBSTITUTED DEOXYADENOSINE DERIVATIVES

[75] Inventors: Philippe Bey, Strasbourg; Michel Jung, Illkirch-Graffenstaden; Michael Kolb, Truchtersheim; Charles Danzin, Strasbourg, all of France

[73] Assignee: Merrell Toraude et Compagnie, Strasbourg, France

[21] Appl. No.: 243,280

[22] Filed: Mar. 13, 1981

[30] Foreign Application Priority Data

Mar. 25, 1980 [GB] United Kingdom ............... 8009995

[51] Int. Cl.³ .................. A61K 31/70; C07H 19/16
[52] U.S. Cl. ........................................ 424/180; 536/26
[58] Field of Search .................... 536/24, 26; 424/180

[56] References Cited

U.S. PATENT DOCUMENTS 3,809,689  5/1974  Damodaran et al. .......... 536/26
4,086,416  4/1978  Acton et al. ..................... 536/24
4,087,603  5/1978  Hamill et al. ................... 536/26

Primary Examiner—Johnnie R. Brown
Attorney, Agent, or Firm—David E. Frankhouser; Raymond A. McDonald; William J. Stein

[57] ABSTRACT

Novel compounds of the following general Formula I are useful pharmacological agents:

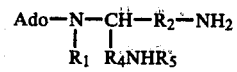

Formula I wherein:
Ado represents 5'-deoxyadenosin-5'-yl;
$R_1$ represents methyl, ethyl or, preferably hydrogen;
$R_2$ represents $C_1-C_8$ alkylene;
$R_4$ represents $C_1-C_8$ alkylene;
$R_5$ represents hydrogen, $C_1-C_6$ alkyl or $-R_6NHR_7$;
$R_6$ represents $C_1-C_4$ alkylene; and
$R_7$ represents hydrogen or $C_1-C_6$ alkyl;

and pharmaceutically acceptable acid addition salts thereof.

16 Claims, No Drawings

SUBSTITUTED DEOXYADENOSINE DERIVATIVES

FIELD OF THE INVENTION

This invention relates to novel pharmaceutically useful 5'-N-substituted amino-5'-deoxyadenosine derivatives which are useful pharmacological agents.

BACKGROUND OF THE INVENTION

The decarboxylation of ornithine to putrescine, a reaction catalysed by the enzyme ornithine decarboxylase (ODC), is the first step in the biosynthesis of the polyamines, spermidine and spermine. Spermidine is formed by the spermidine synthase catalysed transfer of an activated aminopropyl moiety from S-adenosyl S-methyl homocysteamine to putrescine, while spermine is formed by the spermine synthase catalysed transfer of a second aminopropyl group to spermidine. S-adenosyl S-methyl homocysteamine is formed by the decarboxylation of S-adenosylmethionine (SAM), a reaction catalysed by the enzyme S-adenosylmethionine decarboxylase (SAM-DC).

The polyamines, spermidine and spermine, which are found in all animal tissues and certain microorganisms, such as protozoa, are known to play an important role in cell growth and proliferation. The induction of cell growth and proliferation is associated with both a marked increase in ODC activity and an increase in the levels of putresine and the polyamines. Although the exact mechanism of the role of the polyamines in cell growth and proliferation is not known, it appears that the polyamines may facilitate macromolecular processes such as DNA, RNA, or protein synthesis. Polyamine levels are known to be high in embryonic tissue; in the testes, ventral prostate, and thymus; in neoplastic tissue; in psoriatic skin lesions; and in other cells undergoing rapid replication.

Since the polyamines are formed enzymatically, it is seen that inhibition of aminopropyltransferase (i.e. spermidine synthase and/or spermine synthase), can provide a method for regulating the cellular levels of the polyamines. The administration of an aminopropyltransferase inhibitor, thus, can provide a means for controlling the growth of protozoa, wherein the polyamines are important for cell replication, for treating certain disorders associated with rapid cell proliferation (for example, in neoplasms, epidermal hyperplasia, e.g. psoriasis, and prostatic hypertrophy) and for interrupting embrypgenic development (contragestational activity).

It has been proposed in a paper by Coward (Drug Action and Design: Mechanism-Based Enzyme Inhibitors; Elsevier North Holland, 1979 at pages 13 to 26) that aminopropyltransferase would be inhibited by methylsulfonium adducts of the following general Formula A:

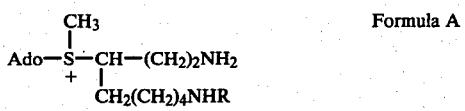

Formula A wherein:

R represents hydrogen or 3-aminopropyl. It is reported in that paper (at page 17) that the adducts had not been prepared but that it was hoped that deblocking and methylation of a totally blocked thioether precursor would yield the compound of Formula A in which R represents hydrogen. In a subsequent paper by Coward and fellow workers (Tang et al, Biochem. Biophys. Research Communications 96, 1371–1377 (1980)) received and published after the priority date of the present application there is reported the inhibition of aminopropyltransferase by an adenosine-5'-thioether of the following Formula B and a corresponding methyl sulfonium salt of the following Formula C:

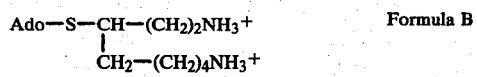

Formula B

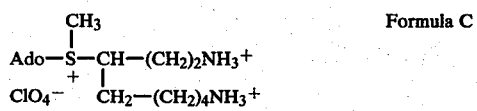

Formula C

It has been reported (Pankaskie and Abdel-Monem, J. Med. Chem. 23, 121–127 (1980)) that a methyl-sulfonium adduct of the following Formula D and the corresponding N-methylamino compound of the following Formula E are inhibitors of SAM-DC:

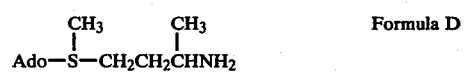

Formula D

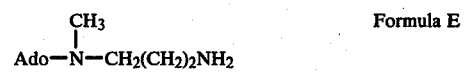

Formula E

SUMMARY OF THE INVENTION

The compounds of the present invention are 5'-N-(aminoalkyl)amino-5'-deoxyadenosines of the following general Formula I:

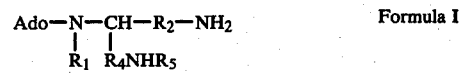

Formula I wherein:
Ado represents 5'-deoxyadenosine-5'-yl;
$R_1$ represents methyl, ethyl or preferably hydrogen;
$R_2$ represents $C_1$–$C_8$ alkylene;
$R_4$ represents $C_1$–$C_8$ alkylene;
$R_5$ represents hydrogen, $C_1$–$C_6$ alkyl or —$R_6NHR_7$;
$R_6$ represents $C_1$–$C_4$ alkylene; and
$R_7$ represents hydrogen or $C_1$–$C_4$ alkyl and pharmaceutically acceptable acid addition salts thereof.

The compounds of the invention are useful in that they are inhibitors of aminopropyltransferase and therefore are capable of depleting levels of spermidine and/or spermine in animal tissues and protozoa. Hence, said compounds are useful for treating those disorders associated with elevated levels of spermidine and/or spermine or pathogenic protozoa.

DETAILED DESCRIPTION OF THE INVENTION

In the above general Formula I, the abbreviation Ado represents 5'-deoxyadenosine-5'-yl which is the univalent radical obtained by removal of the hydroxy group from the 5'-position of adenosine. This radical has the following Formula II:

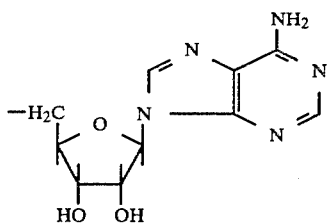

Formula II $R_1$ in general Formula I represents hydrogen, methyl or ethyl and preferably is hydrogen.

$R_2$ in general Formula I represents a straight or branched chain alkylene group having 1 to 8 carbon atoms and preferably is an alkylene group of the formula

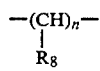

wherein each $R_8$ independently represents hydrogen or methyl; and n represents an integer of 1 to 8, preferably 1 to 4, especially 2. Illustrative examples of the aminoalkyl group —$R_2NH_2$ are aminomethyl, 2-aminoethyl, 3-aminopropyl, 2-amino-1-methylethyl, 3-amino-1,2-dimethylpropyl, 4-aminobutyl, 5-aminopentyl, 6-aminohexyl, 6-amino-1-methylhexyl, 7-aminoheptyl and 8-aminooctyl.

$R_4$ in general Formula I represents straight or branched chain alkylene having 1 to 8 carbon atoms and preferably is an alkylene group of the formula —$(CH_2)_m$— wherein m represents an integer of 3 to 7, especially 5.

$R_5$ in general Formula I represents hydrogen, straight or branched chain alkyl having 1 to 6 carbon atoms or —$R_6NHR_7$, wherein $R_6$ represents straight or branched chain alkylene having 1 to 4 carbon atoms and $R_7$ represents hydrogen or straight or branched chain alkyl having 1 to 4 carbon atoms. Preferably $R_5$ represents hydrogen or —$(CH_2)_pNH_2$, wherein p represents an integer of 2 to 4, especially 3. It is particularly preferred that $R_4NHR_5$ represents —$(CH_2)_mNH(CH_2)_pNH_2$, wherein m and p are as previously defined.

Illustrative examples of alkylene groups $R_4$ are the alkylene groups of the aminoalkyl groups specified above to exemplify the group —$R_2NH_2$. Similarly, illustrative examples of the alkylene groups $R_6$ are said specified alkylene groups having 1 to 4 carbon atoms.

Illustrative examples of alkyl groups represented by $R_5$ and $R_7$ are methyl, ethyl, n-propyl, n-butyl, iso-propyl, sec-butyl and for $R_5$ only, n-pentyl, n-hexyl.

In this Specification, the following general Formula III is sometimes used as an alternative representation of the compounds of Formula I:

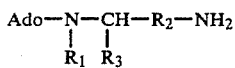

Formula III wherein:
$R_3$ represents $R_4NHR_5$, and
Ado, $R_1$, $R_2$, $R_4$ and $R_5$ are as defined in connection with Formula I. Thus it will be appreciated that Formula III differs from Formula I only insofar as $R_3$ is used to represent $R_4NHR_5$.

In a preferred embodiment of the invention, there are provided 5'-N-(aminoalkyl-amino-5'-deoxyadenosines of the following general Formula IV:

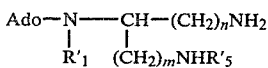

Formula IV wherein:
Ado represents 5'-deoxyadenosin-5'-yl;
$R_1'$ represents methyl or, preferably hydrogen;
$R_5'$ represents hydrogen or —$(CH_2)_pNH_2$;
n represents an integer of 1 to 4, especially 2;
m represents an integer of 3 to 7, especially 5; and
p represents an integer of 2 to 4, especially 3,
and pharmaceutically acceptable acid addition salts thereof.

The compounds of Formula I are optically active and the present invention includes not only racemates and other mixtures of the optical isomers but also the individual optical isomers. Methods of selecting reactants and/or optically resolving intermediates to provide a desired individual optical isomer are well known per se to those skilled in the art. Usually, the deoxyadenosinyl group will be in the D-configuration and is in that configuration in all the Examples of this Specification. In this connection, there is no optical significance in the manner in which deoxyadenosinyl group has been shown in the various formulae of this Specification.

Illustrative examples of compounds of the invention are the following:

5'-N-(6-amino-1(2-aminoethyl)hexyl)amino-5'-deoxyadenosine ($R_1$=H; $R_2$=—$CH_2CH_2$—; $R_3$=$(CH_2)_5NH_2$);

5'-N-methyl-N-(6-amino-1(2-aminoethyl)hexyl)-amino-5'-deoxyadenosine ($R_1$=$CH_3$; $R_2$=—$CH_2CH_2$—; $R_3$=—$(CH_2)_5NH_2$);

5'-N-(6-(N'-3-aminopropyl)amino-1-(2-amino-ethyl)hexyl)amino-5'-deoxyadenosine ($R_1$=H, $R_2$=—$CH_2CH_2$—; $R_3$=—$(CH_2)_5NH(CH_2)_3NH_2$;

5'-N-methyl-N-(6-(N'-3-aminopropyl)amino-1-(2-aminoethyl)hexyl)amino-5'-deoxyadenosine ($R_1$=$CH_3$; $R_2$=—$CH_2CH_2$—; $R_3$=—$(CH_2)_5NH(CH_2)_3NH_2$);

5'-N-(6-(N'-methyl)amino-1-(2-aminoethyl)hexyl)amino-5'-deoxyadenosine ($R_1$=H; $R_2$=—$CH_2CH_2$—; $R_3$=—$(CH_2)_5NHCH_3$); and 5'-N-(6-(N'-(N''-methyl)3-aminopropyl)amino-1-(2-aminoethyl)hexyl)amino-5'-deoxyadenosine ($R_1$=H; $R_2$=—$CH_2CH_2$—; $R_3$=—$(CH_2)_5NH(CH_2)_3NHCH_3$).

The compounds of Formula I inhibit spermidine and/or spermine synthase and can, therefore, block the biosynthesis of spermidine and spermine. Hence, the compounds can be employed for controlling undesirable cell proliferation, and pathogenic protozoa which cause parasitic infections in domestic animals and humans.

The utility of the compounds as inhibitors of spermidine and spermine synthase can be demonstrated in vitro by measuring the time taken to double the cell population of HTC cells in culture in the presence of the relevant compound compared with otherwise identical conditions but in the absence of the relevant compound.

The term "controlling" when employed with respect to the term "pathogenic protozoa", as used herein, means slowing, arresting, or stopping the replication of the protozoa either in vitro or in vivo. The compounds of Formula I will be useful against *T.b. brucei* (which causes trypanosomiasis in cattle) and the coccidia, for example, *Eimeria tenella* (which causes coccidiosis in chickens). The antiprotazoal activity of the compounds of Formula I can be demonstrated in vivo or in vitro in standard microbiological test procedures. For example, the activity of the compounds against *T.b. brucei* can be determined in infected mice by administering the test compound ad lib daily (3 to 15 days post infection) as a solution in the drinking water at a concentration of 0.5 to 2%. Activity is indicated by an increase in survival time (as compared to untreated controls) or by assaying blood samples for parasites. The activity of the compounds against the coccidia can be determined in infected chickens, for example those infected with *E. tenella* by administering the test compound daily ad lib (from the one day pre injection to 5 days post infection) as a solution in the drinking water at a concentration of 0.5 to 2%. [See Reid, *Am. J. Vet Res.*, 30, 447 (1969) and *Avian Coccidiosis*, P. Long. Editor, British Poultry Science, Ltd., Edinburgh]. The cecal lesions are evaluated by a standard lesion scoring procedure.

The compounds of this invention can be administered in various manners to achieve the desired effect. The compounds can be administered alone or in the form of pharmaceutical preparations to the patient being treated either orally or parenterally, for example, subcutaneously, intravenously or intraperitoneally. The amount of novel compound administered will vary and can be any effective amount. Depending upon the patient, the condition being treated and the mode of administration, the quantity of novel compound administered may vary over a wide range to provide from about 0.1 mg/kg (milligram per kilogram) to about 50 mg/kg of body weight of the patient per day. Unit doses of these compounds can contain, for example, from about 1 mg to 100 mg of the compound and may be administered, for example, from 1 to 4 times daily.

As used herein the term patient is taken to mean warm blooded animals, such as mammals, for example, cats, dogs, rats, mice, guinea pigs, sheep, horses, bovine cows and humans.

The term "unit dosage form" is used herein to mean a physically discrete unit containing an individual quantity of the active ingredient in admixture with or otherwise in association with the carrier, said quantity being such that one or more units are normally required for a single therapeutic administration or that, in the case of severable units such as scored tablets, at least one fraction such as a half or quarter of a severable unit is required for a single therapeutic administration.

In the composition aspect of the invention there are provided pharmaceutical formulations in which form the active compounds of the invention will normally be utilized. Such formulations are prepared in a manner well known per se in the pharmaceutical art and usually comprise at least one active compound of the invention in admixture or otherwise in association with a pharmaceutically acceptable carrier or diluent therefor. For making these formulations the active ingredient will usually be mixed with a carrier, or diluted by a diluent, or enclosed or encapsulated in a capsule, sachet, cachet, paper or other container. A carrier or diluent may be solid, semi-solid or liquid material which serves as a vehicle, excipient or medium for the active ingredient. Suitable diluents or carriers are well known per se.

The formulations of the invention may be adapted for enteral or parenteral use and may be administered to the patient in the form of tablets, capsules, suppositories, solutions, suspensions or the like.

In the specific Examples included hereinbelow illustrative examples of suitable pharmaceutical formulations are described.

Compounds of Formula I can be prepared by contacting in manner known per se 5'-bromo-, chloro- or tosyl-5'-deoxyadenosine with the corresponding amine of the following general Formula V:

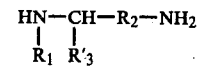

Formula V wherein:

$R_1$ and $R_2$ are as defined in connection with Formula I and $R_3'$ is as defined for $R_3$ in connection with Formula I and $R_3'$ is as defined for $R_3$ in connection with Formula III except that the amine group is protected against alkylation by a subsequently removable blocking group or groups. The reaction can be carried out in the absence of a solvent at a temperature in the range of about 10° C. to about 50° C. for from about 1 day to about 8 days in the dark and using about 20 to about 40 equivalents of amine per equivalent of 5'-chloro-5'-deoxyadenosine. The 5'-bromo- or chloro-5'-deoxyadenosine reactant can be obtained by the methods reported by Kikugawa et al (Tetrahedron Letters, 1971, 87) and Gibbs et al (Synth. Comm. (1976) 6, 503). 5'-Tosyl-5'-deoxyadenosine is also a known compound.

Suitable blocking groups for any amine group in $R_3'$ are, for example, those forming phthalimido or carbamate, especially t-butyl or benzyl carbamate, with an amino group. These blocking groups can be introduced or the relevant blocked compounds obtained in manner known per se and the blocking groups can be removed in manner known per se.

Compounds of Formula I can also be prepared from 2',3'-hydroxy protected 5'-amino-5'-deoxyadenosine (Formula VIII below) and the corresponding halogenated alkanol of the following general Formula VI:

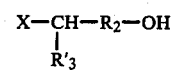

Formula VI wherein:

$R_2$ is as defined in connection with Formula I, $R_3'$ is as defined for $R_3$ in connection with Formula III except that the amine group is protected against alkylation by a subsequently removable blocking group or groups, and X represents chlorine, bromine or iodine.

The hydroxy groups at the 2' and 3' positions of the 5'-amino-5'-deoxyadenosine are protected against alkylation with a blocking group or groups, such as, for example, an alkylidene or alkoxymethylidene group. These blocking groups can be introduced into 5'-amino-5'-deoxyadenosine (a known compound) in manner known per se. However, it is more usual to protect the 2' and 3' hydroxy groups of adenosine (see Formula VII) and then introduce the 5'-amino group in manner known per se.

The 2',3'-hydroxy-protected 5'-amino-5'-deoxyadenosine (Formula VIII below) is converted in manner known per se by reaction with the halogenated alkanol of Formula VI into the corresponding 2',3'-hydroxy-protected 5'-(hydroxyalkyl)amino-5'-deoxyadenosine (Formula IX below). This 5'-(hydroxyalkyl)-amino-5'-deoxyadenosine derivative (Formula IX) is then converted in manner know per se by reaction with phthalimide in the presence of a trialkyl- or triarylphosphine and diethyldiazenedicarboxylate into the corresponding 5'-(phthalimidoalkyl)amino-5'-deoxyadenosine (Formula X below) which is subsequently converted in manner known per se by reaction with a reactant such as hydrazine or methylamine into the corresponding 2',3'-hydroxy-protected-5'-(aminoalkyl)amino-5'-deoxyadenosine (Formula XI below). Removal of the 2' and 3' hydroxy blocking group(s) and of any amino blocking group of $R_3'$ in manner known per se yields the desired compound of Formula III. For example an alkylidene or alkoxymethylidene blocking group can be removed by acidification and the resultant acid addition salt is then neutralized. The reaction sequence can be represented as follows:

ing group is 1-methylethylidene, in which case the 2',3'-hydroxy-protected-5'-amino-5'-deoxyadenosine of Formula VIII has the following Formula VIIIa:

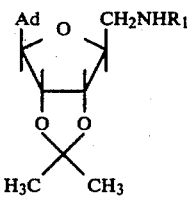

Formula VIIIa wherein
Ad represents adenin-9-yl and
$R_1$ is as defined in connection with Formula I.

The reaction between the halogenated alkanol of Formula VI and the 2' and 3'hydroxy-protected 5'-

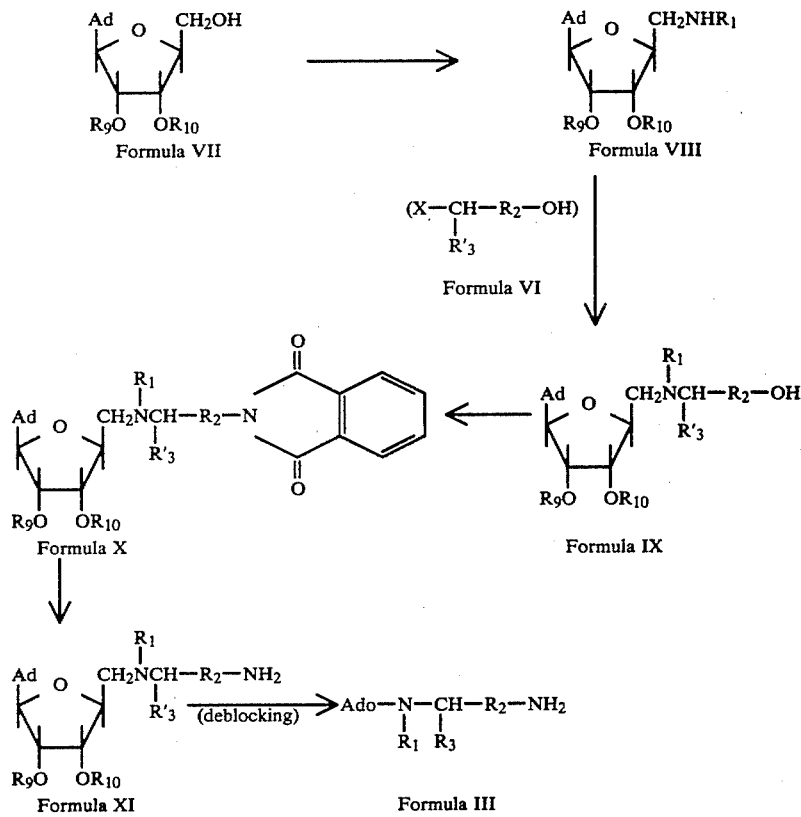

In the reaction sequence above:
Ad represents adenin-9-yl;
Ado, $R_1$, $R_2$ and $R_3$ are as defined in connection with Formula I;
$R_3'$ is as defined for $R_3$ in connection with Formula III except that the amine group is protected against alkylation by a subsequently removable blocking group or groups; and
$R_9$ and $R_{10}$ independently represent blocking groups or together represent a single blocking group protecting both 2'- and 3'-hydroxy groups.

Suitably $R_9$ and $R_{10}$ together represent an alkylidene group or an alkoxymethylidene group. Illustrative examples of suitable alkylidene groups are 1-methylethylidene, cyclohexylidene and benzylidene and illustrative examples of alkoxymethylidene groups are methoxymethylidene and ethoxymethylidene. The preferred blockamino-5'-deoxyadenosine of Formula VIII can be carried out in manner known per se in an anhydrous aprotic organic solvent and in the presence of a tertiary amine. Suitable solvents are, for example, pyridine, acetonitrile, dimethylsulfoxide, and dialkylamides, e.g. dimethylacetamide and dimethylformamide. Suitable tertiary amines are, for example, aromatic cyclic amines, especially pyridine and quinoline, and trialkylamines, especially triethylamine. The reaction temperature can be in the range of about $-5°$ C. to about $+5°$ C. for about five minutes and then in the range of about $10°$ C. to about $50°$ C. for about 24 hours. The halogenated alkanol, aminodeoxyadenosine and tertiary amine usually will be present in an equivalents ratio of 1:1:1. In a preferred embodiment, said reactants and amine are present in about 0.5 molar concentration in dimethylformamide.

The reaction between the 2' and 3' hydroxy-protected 5'-(hydroxyalkyl)amino-5'-deoxyadenosine and phthalimide (i.e. 1,3-dihydro-1,3-dioxo-2H-isoindole) also can be carried out in manner known per se in an anhydrous aprotic solvent in the presence of diethyl-diazenedicarboxylate and a trialkyl- or triaryl-phosphine, for example triphenylphosphine. Suitable aprotic solvents are, for example, ethers, e.g. diethylether, tetcompound (Formula XIIa below) to form the corresponding protected azomethine derivative (Formula XIV below) which is reduced to the corresponding amino and hydroxy-protected 5'(amino-alkyl)amino-5'-deoxyadenosine (Formula XV below) and then the amino and hydroxy groups are freed to yield the desired compound of Formula I. The reaction sequence can be represented as follows:

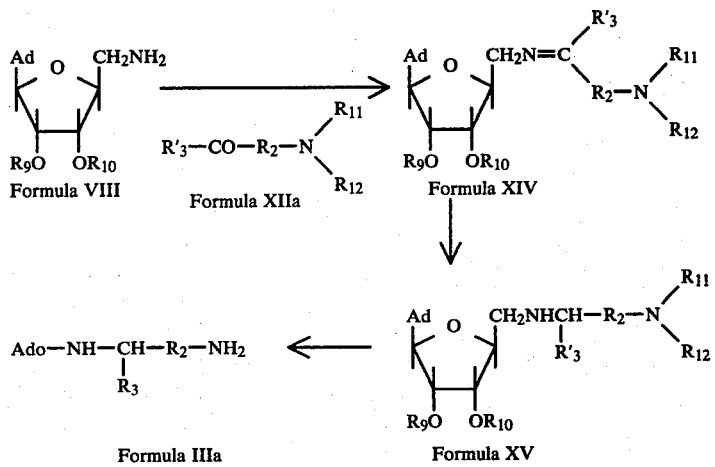

rahydrofuran and diglyme; aliphatic hydrocarbons, e.g. pentane, hexane, octane and decane; and aromatic hydrocarbons, e.g. benzene and toluene. Usually, the reaction is conducted with 1 to 3 equivalents each of phthalimide, trialkyl- or triaryl-phosphine and diethyldiazenedicarboxylate per equivalent of hydroxyalkylaminodeoxyadenosine and at a temperature in the range of about 10° C. to about 100° C. for a time of about 18 hours to about 24 hours. In a preferred embodiment, the reactants are present in about 0.5 to about 1 molar concentration in tetrahydrofuran.

The 2' and 3' hydroxy-protected-5'-(phthalimidoalkyl)-amino-5'-deoxyadenosine can be converted in manner know per se into the corresponding 2' and 3' hydroxy-protected-5'-(aminoalkyl)amino-5'-deoxyadenosine by reaction with a reactant such as hydrazine or methylamine in a polar organic solvent. Preferably hydrazine hydrate is used in an amount of about 2 to about 50 equivalents per equivalent of the deoxyadenosine reactant. Suitable solvents are, for example, alkanols, e.g. methanol, ethanol, n-propanol, iso-propanol, or n-butanol with ethanol being the preferred solvent. The conversion can be performed at a temperature in the range of about 50° C. to about 100° C., preferably under reflux conditions, for a period of about 3 to 24 hours. Following the conversion, the 2' and 3' hydroxy groups and any protected amine group are freed by removal of the blocking group(s) in manner known per se.

A further method of obtaining compounds of the general Formula I commences from 2',3'-hydroxy-protected-5'-amino-5'-deoxyadenosine of Formula VIII and an aldehyde or ketone of the following general Formula XII:

R$_3$-CO-R$_2$-NH$_2$   Formula XII

Each amino group of the carbonyl compound of Formula XII is protected by introducing a suitable blocking group. The deoxyadenosine derivative of Formula VIII is then contacted with the amino-protected carbonyl In the reaction sequence above:
Ad represents adenin-9-yl;
Ado, R$_2$ and R$_3$ are as defined in connection with Formula I;
R$_3$' is as defined for R$_3$ in connection with Formula III except that the amine group is protected against alkylation by a subsequently removable blocking group or groups;
R$_9$ and R$_{10}$ independently represent blocking groups or together represent a single blocking group protecting both 2' and 3'-hydroxy groups; and
R$_{11}$ represents a blocking group or hydrogen and R$_{12}$ represents a blocking group or R$_{11}$ and R$_{12}$ together represent a blocking group.

Suitable blocking groups for the or each amine are, for example, those forming a phthalimido or carbamate, especially t-butyl or benzyl carbamate, with the amino group. These blocking groups can be introduced or the relevant blocked compounds obtained in manner known per se.

The reaction between the 5'-amino-5'-deoxyadenosine derivative of Formula VIII and the carbonyl derivative of Formula XIIa can be carried out in manner known per se in a protic solvent for example an alcohol or water. It is preferred that the reaction is carried out with one equivalent of the carbonyl derivative per equivalent of the deoxyadenosine derivative and at a temperature in the range of about 10° C. to about 50° C. for a period of about 1 hour to about 10 hours. In a preferred embodiment of the method, the reactants are reacted at about 0.2 molar concentration in methanol.

The reduction of the deoxyadenosine derivative can be carried out in manner known per se with a mild reducing agent such as, for example, a borohydride, e.g. sodium or lithium borohydride, in an alcohol, e.g. methanol. The pH of the solution preferably is adjusted to pH 7 by the addition of acid, for example acetic acid. Usually, 5 to 100 equivalents of the borohydride will be used per equivalent of the deoxyadenosine reactant and the reaction temperature will be in the range of about −5° C. to about +5° C. for about 10 minutes and then in the range of about 10° C. to about 30° C. for a period of about 1 hour to about 3 hours.

The amino- and hydroxy-protecting groups are removed in manner known per se and said removal of protecting groups has been discussed above.

In the case of a phthalimido group, the amino group can be freed by treatment with a reactant, such as hydrazine or methylamine whilst, in the case of a t-butyl or benzyl carbamate group, the amino group can be freed by treatment with acid, for example hydrogen chloride gas. The reaction conditions for hydrazine or methylamine treatment have been discussed above with reference to production of compounds of Formula XI. In the case of t-butyl or benzyl carbamate groups, the carbamate can be contacted in solution in an organic solvent such as acetic acid with hydrogen chloride gas. Usually about 3 to 10 equivalents of hydrogen chloride are used per equivalent of carbamate and at a temperature in the range of about 10° C. to about 30° C. for a period of about 0.5 hours to about 3 hours.

Certain compounds of Formula I can be prepared from a 2',3'-hydroxy-protected 5'-amino-5'-deoxyadenosine of Formula XIII and a cyanoalkene of the following general Formula XVI:

Formula XVI wherein:

$R_{13}$ is hydrogen or a $C_1-C_7$ alkyl group; and $R_3'$ is as defined for $R_3$ in connection with Formula III except that the amine group is protected with a subsequently removable blocking group.

The said reactants of Formula XIII and XVI are contacted to form the corresponding 5'-(cyanoalkyl)amino-5'-deoxyadenosine (Formula XVII below) which is then reduced to the corresponding 2',3'-hydroxy-protected 5'-(aminoalkyl)amino-5'-deoxyadenosine (Formula XVa below) and the 2' and 3'-hydroxy groups and if present protected amine group are subsequently freed. The reaction sequence can be represented as follows:

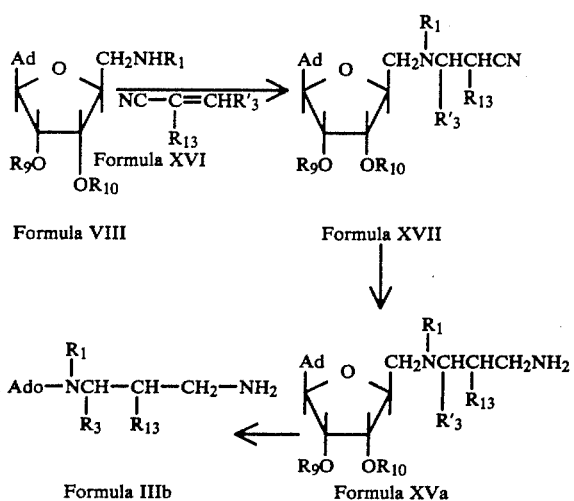

In the reaction sequence above:

Ad represents adenin-9-yl;

Ado, $R_1$ and $R_3$ are as defined in connection with Formula I;

$R_3'$ is as defined for $R_3$ in connection with Formula III except that the amine group is protected against alkylation by a subsequently removable blocking group or groups;

$R_9$ and $R_{10}$ independently represent blocking groups or together represent a single blocking group protecting both 2' and 3'-hydroxy groups; and $R_{13}$ represents hydrogen or a $C_1-C_7$ alkyl group.

The reaction between the compound of Formulae VIII and XVI can be carried out in manner known per se in a polar solvent, for example an alcohol or water. Suitable alcohols are, for example, methanol, ethanol, n-propanol, iso-propanol, and n-butanol. Usually one equivalent of the cyanoalkene compound of Formula XVI will be used per equivalent of the deoxyadenosine compound for Formula VIII and at a reaction temperature in the range of about 10° C. to about 50° C. for a period of about 18 hours to about 3 days. In a preferred embodiment, a 2 molar solution of the reactants in water is used.

The reduction of the cyanoalkylaminodeoxyadenosine of Formula XVII can be carried out in manner known per se using a mild reducing agent, such as hydrogen and a Raney Ni catalyst and an alcohol solvent saturated with ammonia. Suitably the alcohol is ethanol and a hydrogen pressure of about 10 to about 150 atmospheres, especially about 120 atmospheres, is used. The reaction temperature can be in the range of about 100° C. to about 150° C. for a period of about 24 to about 48 hours.

Certain compounds of Formula I also can be prepared from a 2',3'-hydroxy-protected 5'-amino-5'-deoxyadenosine of Formula VIII and an alkene carboxylic acid alkyl ester of the following general Formula XVIII:

Formula XVIII wherein:

$R_3'$ and $R_{13}$ are as defined in connection with Formula XVI; and $R_{14}$ is a $C_1-C_{10}$ straight or branched chain alkyl group.

The compounds of Formulae VIII and XVIII react to form the corresponding 5'(alkoxycarbonylalkyl)amino-5'-deoxyadenosine (Formula XIX below) which is then reduced to the corresponding 5'(hydroxyalkyl)amino-5'-deoxyadenosine (Formula XX below). The hydroxyalkylaminodeoxyadenosine is subsequently converted into the corresponding 5'(phthalimidoalkyl)-amino-5'-deoxyadenosine (Formula Xa below) which is treated with a reactant such as hydrazine or methylamine to form the corresponding 5'(aminoalkyl)amino-5'-deoxyadenosine (Formula XIa below) from which the blocking groups are then removed to form the desired compound of Formula I. The reaction sequence can be represented as follows:

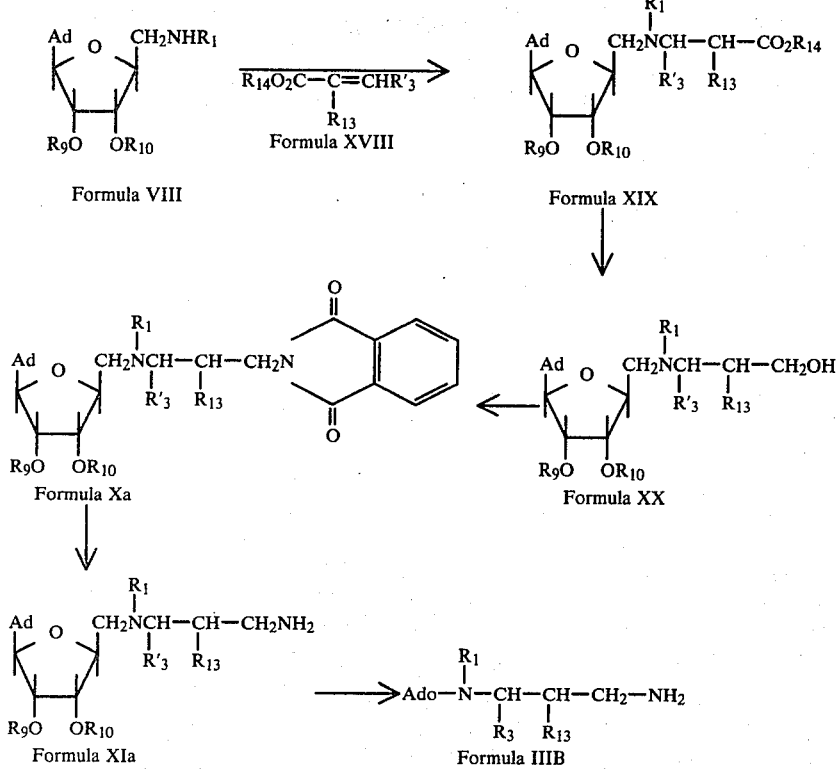

In the reaction sequence above:

Ad represents adenin-9-yl;

Ado, $R_1$ and $R_3$ are as defined in connection with Formula I;

$R_3'$ is as defined for $R_3$ in connection with Formula III except that the amine group is protected against alkylation by a subsequently removable blocking group or groups;

$R_9$ and $R_{10}$ independently represent blocking groups or together represent a single blocking group protecting both 2′ and 3′-hydroxy groups; and $R_{13}$ represents hydrogen or a $C_1$–$C_7$ alkyl group.

The reaction between the compounds of Formulae VIII and XVIII can be carried out in manner known per se in a polar solvent, for example an alcohol or water. Suitable alcohols are, for example, methanol, ethanol, n-propanol, iso-propanol and n-butanol. Usually, one equivalent of the ester of Formula XVIII will be used per equivalent of deoxyadenosine compound of Formula VIII and at a reaction temperature in the range of about 10° C. to about 50° C. for a period of about 18 hours to about 3 days. In a preferred embodiment a 3 molar solution of the reactants in methanol is preferred.

The reduction of the alkoxycarbonylalkylaminodeoxyadenosine of Formula XIX can be carried out in manner known per se using a mild reducing agent such as a dialkylaluminiumhydride, especially diisobutylaluminiumhydride, in an anhydrous aprotic organic solvent. Suitable solvents are, for example, esters, e.g. diethylether, tetrahydrofuran and diglyme; aromatic hydrocarbons, e.g. benzene and toluene; and chlorinated aliphatic hydrocarbons, e.g. dichloromethane and chloroform. Usually, the reaction is conducted with 3 to 10 equivalents of dialkylaluminiumhydride per equivalent of alkoxycarbonylalkylaminodeoxyadenosine and at a temperature in the range of about −80° C. to about +20° C. for a time of about 1.5 hours to about 3 hours.

In a preferred embodiment, the reactants are present in about 0.25 molar concentration in tetrahydrofuran.

The conversion of the hydroxyalkylaminodeoxyadenosine of Formula XX to the phthalimidoalkylaminodeoxyadenosine of Formula Xa can be carried out in manner known per se by reaction with phthalimide in an anhydrous aprotic solvent in the presence of diethyldiazenedicarboxylate and a trialkyl- or triaryl phosphine. The reaction conditions are as discussed above with reference to the preparation of compounds of Formula X.

The phthalimidoalkylaminodeoxyadenosine of Formula Xa can be converted to the corresponding 2′,3′-hydroxy-protected-5′(aminoalkyl)amino-5′-deoxyadenosine of Formula XIa in manner known per se by treatment with a reactant such as hydrazine or methylamine in a polar organic solvent. The reaction conditions are as discussed above with reference to the preparation of compounds of Formula XI. The product of Formula XIa is subsequently treated to free the protected amino and hydroxy groups by removal of the respective blocking groups, which removal has been discussed with reference to the preparation of compounds of Formula Ia from compounds of Formula XI.

The hydroxyalkylamino-5′-deoxyadenosines of Formula IX can be obtained by contacting in manner known per se the 2′,3′-hydroxy-protected aminodeoxyadenosine of Formula VIII with an aldehyde or ketone of the following Formula XXI and subsequently reducing in manner known per se the resultant azomethinedeoxyadenosine of the following Formula XXII. The reaction sequence can be represented as follows:

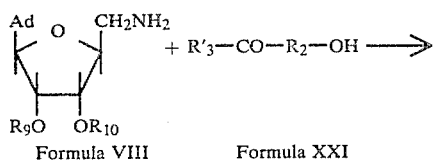

Formula VIII    Formula XXI

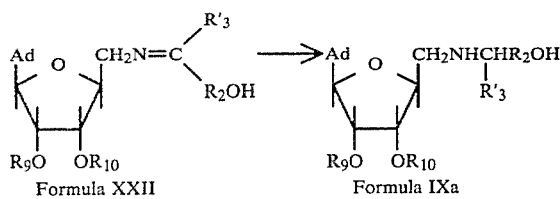

Formula XXII    Formula IXa

In the reaction sequence above:
Ad represents adenin-9-yl;
$R_2$ is as defined in connection with Formula I;
$R_3'$ is as defined for $R_3$ in connection with Formula III except that the amine group is protected against alkylation by a subsequently removable blocking group or groups; and
$R_9$ and $R_{10}$ independently represent blocking groups or together represent a single blocking group protecting both 2'- and 3'-hydroxy groups.

The reaction between the compounds of Formulae VIII and XXI can be carried out in manner known per se using the reaction conditions described above for the reaction between compounds of Formulae VIII and XIIa. Similarly, the reduction of the compound of Formula XXII can be carried out in manner known per se using the reaction conditions described above for the reduction of a compound of Formula XIV. The compound of Formula VIIIa can be converted into a compound of Formula IIIa by the same procedure used to convert a compound of Formula XX into a compound of Formula IIIa.

The compounds produced by the foregoing processes may be isolated either per se or as acid addition salts thereof. The acid addition salts are preferably the pharmaceutically acceptable, non-toxic addition salts with suitable acids, such as those with inorganic acids, for example hydrochloric, hydrobromic, nitric, sulfuric or phosphoric acids, or with organic acids, such as organic carboxylic acids, for example, glycollic, maleic, hydroxymaleic, malic, tartaric, citric, salicyclic, o-acetyloxybenzoic, nicotinic or isonicotinic, or organic sulphonic acids for example methane sulphonic, ethane sulphonic, 2-hydroxyethane sulphonic, toluene-p-sulphonic, or naphthalene-2-sulphonic acids. Apart from pharmaceutically acceptable acid addition salts, other salts are also included within the scope of acid addition salts, such as for example, those with picric or oxalic acid; they may serve as intermediates in the purification of the compounds or in the preparation of other, for example, pharmaceutically acceptable, acid addition salts, or are useful for identification or characterisation of the bases.

A resulting acid addition salt may be converted into the free compound or into another acid addition salt according to known methods.

The invention is illustrated in the following non-limiting Examples.

EXAMPLE 1

5'-N-[6-Amino-1-(2-aminoethyl)hexyl]amino-5'-deoxyadenosine (a) t-Butyl-(6-hydroxyhexyl)carbamate

A solution of 6-amino-1-hexanol (3.51 g, 0.03 mol) in chloroform (6 ml) is treated with potassium hydrogen carbonate (3 g in 6 ml of water) and di-t-butyl-dicarbonate (6.55 g, 0.03 mol) for 14 hours at room temperature. After adding 5 ml water, t-butyl-(6-hydroxyhexyl)carbamate is extracted from the reaction mixture with chloroform (5.88 g, 80%).

(b) t-Butyl-(5-formylpentyl)carbamate

Pyridinium dichromate (13.5 g, 0.036 mol) is added to a solution of t-butyl-(6-hydroxyhexyl)carbamate (5.88 g, 24 mmol) in dichloromethane (40 ml). After stirring for 24 hours, the reaction mixture is diluted with diethylether/pentane (1:1), filtered through Florisil and concentrated to yield t-butyl-(5-formylpentyl)carbamate (4.13 g, 80%).

(c) t-Butyl-(7-cyano-hepten-6-yl)carbamate

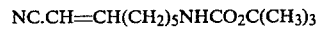

Sodium hydride (50% suspension in oil, 1.2 g, 0.025 mol) is placed in 100 ml of dry 1.2-dimethoxyethane. The slurry is cooled to 20° C. and diethylcyanomethyl phosphonate (4.43 g, 0.025 mol) is added dropwise with stirring. After the addition, the solution is stirred at room temperature for 1 hour until gas evolution has ceased. To the yellow solution, maintained below 25° C., is added dropwise t-butyl(5-formylpentyl)carbamate (5.38 g, 0.025 mol). The solution is stirred at room temperature for 1 hour and refluxed for 0.5 hour. A large excess of water is added and the product t-butyl-(7-cyanohepten-6-yl)carbamate (3.63 g, 61%) is extracted with ether.

(d) 5'-Phthalimide-2',3'-(1-methylethylidene)5'-deoxyadenosine

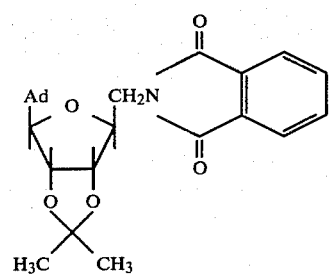

To a mixture of 2',3'-(1-methylethylidene)-adenosine (5.5 g, 0.018 mol), triphenylphosphine (4.7 g, 0.018 mol) and phthalimide (2.65 g, 0.018 mol) in tetrahydrofuran (50 ml, distilled from lithium aluminium hydride) under nitrogen is added, slowly at room temperature, diethyldiazenedicarboxylate (3.15 g, 0.018 mol). After 5–10 minutes a colourless solid precipitates from the orange solution. After 2 hours at room temperature the mixture is filtered and the solid obtained is washed three times with diethyl-ether (50 ml) to give 5'-(phthalimido)-2',3'-(1-methylethylidene)-5'-deoxyadenosine (6.3 g, 80%).

(e) 5'-Amino-2',3'-(1-methylethylidene)-5'-deoxyadenosine

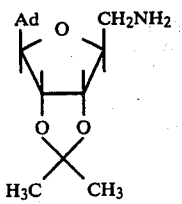

A solution of 5'-(phthalimide)-2',3'-(1-methylethylidene)-5'-deoxyadenosine (5.23 g, 0.013 mol) in ethanol (1.3 liters) and hydrazine hydrate (9 g, 0.189 mol) is refluxed for 18 hours and then cooled to room temperature. The resultant precipitate is filtered off and the organic layer concentrated under vacuo to give a white solid, which is dissolved in water (150 ml) and then acetic acid added to pH 4 to yield a precipitate, which is removed by filtration. The filtrate is concentrated to 50 ml, basified by addition of sodium hydroxide (1 N in water) to pH 11 and extracted five times with chloroform (50 ml). The organic layer is dried over $Na_2SO_4$ and removed under vacuo to yield 5'-amino-2',3'-(1-methylethylidene)-5'-deoxyadenosine (3.71 g, 93%).

(f) 5'-N-[6-Amino-1-(2-aminoethyl)hexyl]amino-5'-deoxyadenosine

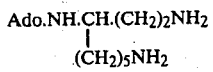

A solution of 5'-amino-2',3'-(1-methylethylidene)-5'-deoxyadenosine (4.6 g, 0.015 mol) and t-butyl-(7-cyanohepten-6-yl)carbamate (3.57 g, 0.015 mol) in methanol (5 ml) is stirred at room temperature in the dark for 18 hours. After removal of methanol under vacuo, an oily residue is obtained. The residue is dissolved in absolute alcohol (30 ml) saturated with ammonia and a Raney/Ni catalyst is added. After hydrogenation in a pressure vessel at 120° C. and 120 atmospheres for 24 hours the reaction mixture is filtered and concentrated under vacuo to give a yellowish oil. An aqueous solution of the oily residue is applied to an ion-exchange resin DOWEX 50, $NH_4^+$ form. After extensive washing with 1 l water, 1 l 0.1 N $NH_4OH$ and 500 ml 1 N $NH_4OH$, the product is eluated from the resin with 1 liter 6 N $NH_4OH$. Lyophilisation of the product-containing fractions gives a white foam which is dissolved in 50 ml 1 N HCl. After 10 hours the solution is extracted with diethylether, and lyophilised to yield a white residue, which is subsequently recrystallised from methanol to yield 5'-N-[6-amino-1-(2-aminoethyl)-hexyl]amino-5'-deoxyadenosine dihydrochloride. An aqueous solution of the dihydrochloride salt is basified by addition of DOWEX 1 ($OH^-$ form) and the resultant mixture is filtered and lyophilised to yield the corresponding free base.

EXAMPLE 2

The procedure of Example 1 is repeated using 0.03 mol of a respective aminoalkanol instead of 6-amino-1-hexanol in step (a) to yield the following aminoalkylaminodeoxyadenosines 5'-N-(2-amino-1-(2-aminoethyl)ethyl)amino-5'-deoxyadenosine (aminoalkanol=2-amino-1-ethanol)

5'-N-(3-amino-1-(2-aminoethyl)propyl)amino-5'-deoxyadenosine (aminoalkanol=3-amino-1-propanol)

5'-N-(4-amino-1-(2-aminoethyl)butyl)amino-5'-deoxyadenosine (aminoalkanol=4-amino-1-butanol)

5'-N-(5-amino-1-)2-aminoethyl)pentyl)amino-5'-adenosine (aminoalkanol=5-amino-1-pentanol)

5'-N-(7-amino-1-(2-aminoethyl)heptyl)amino-5'-adenosine (aminoalkanol=7-amino-1-heptanol)

5'-N-(8-amino-1-(2-aminoethyl)octyl)amino-5'-adenosine (aminoalkanol=8-amino-1-octanol)

5'-N-(9-amino-1-(2-aminoethyl)nonyl)amino-5'-adenosine (aminoalkanol=9-amino-1-nonanol).

In the following Examples relating to pharmaceutical compositions, the term "active compound" is used to indicate the compound 5'-N-(6-amino-1-(2-aminoethyl)-hexyl)amino-5'-deoxyadenosine. This compound may be replaced in these compositions by any other compound of the invention, for example by any of those referred to in Example 2. Adjustments in the amount of medicament may be necessary or desirable depending upon the degree of activity of the medicament as is well known in the art.

EXAMPLE 3

An illustrative composition for hard gelatin capsules is as follows:

| (a) active compound | 20 mg |
|---|---|
| (b) talc | 5 mg |
| (c) lactose | 90 mg |

The formulation is prepared by passing the dry powders of (a) and (b) through a fine mesh screen and mixing them well. The powder is then filled into hard gelatin capsules at a net fill of 115 mg per capsule.

EXAMPLE 4

An illustrative composition for tablets is as follows:

| (a) active compound | 20 mg |
|---|---|
| (b) starch | 43 mg |
| (c) lactose | 45 mg |
| (d) magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 5

An illustrative composition for an injectable suspension is the following 1 ml ampul for an intramuscular injection:

| | weight percent |
|---|---|
| (a) active compound | 1.0 |
| (b) polyvinylpyrrolidone | 0.5 |
| (c) lecithin | 0.25 |
| (d) water for injection to give | 100.0 |

The materials (a)–(d) are mixed, homogenized, and filled into 1 ml ampuls which are sealed and autoclaved 20 minutes at 121° C. Each ampul contains 10 mg per ml of novel compound (a).

EXAMPLE 6

|  | mg/suppositary |
| --- | --- |
| Active Compound | 50 |
| Oil of Theobroma | 950 |

The medicament is powdered and passed through a B.S. No. 100 Sieve and triturated with molten oil of Theobroma at 45° C. to form a smooth suspension. The mixture is well stirred and poured into moulds each of nominal 1 G capacity, to produce suppositories.

What is claimed is:

1. A 5'-N-(aminoalkyl)amino-5'-deoxyadenosine of the formula $$\text{Ado}-\underset{R_1}{\overset{|}{N}}-\text{CH}-\underset{R_4NHR_5}{\overset{|}{R_2}}-\text{NH}_2$$

wherein:
Ado represents 5'-deoxyadenosine-5'-yl;
$R_1$ represents hydrogen, methyl or ethyl;
$R_2$ represents $C_1$-$C_8$ alkylene;
$R_4$ represents $C_1$-$C_8$ alkylene;
$R_5$ represents hydrogen, $C_1$-$C_6$ alkyl or —$R_6NHR_7$;
$R_6$ represents $C_1$-$C_4$ alkylene; and
$R_7$ represents hydrogen or $C_1$-$C_4$ alkyl or a pharmaceutically acceptable acid addition salt thereof.

2. A compound as claimed in claim 1 wherein $R_1$ represents hydrogen.

3. A compound as claimed in claim 1 wherein $R_2$ represents $$-(\underset{R_8}{\overset{|}{CH}})_n-,$$

each $R_8$ independently represents hydrogen or methyl and n represents an integer of 1 to 4.

4. A compound as claimed in claim 1 wherein $R_4$ represents —$(CH_2)_m$— and m represents an integer of 3 to 7.

5. A compound as claimed in claim 1 wherein $R_5$ represents hydrogen.

6. A compound as claimed in claim 1 wherein $R_5$ represents —$(CH_2)_pNH_2$ and p represents an integer of 2 to 4.

7. A 5'-N-(aminoalkyl)amino-5'-deoxyadenosine as claimed in claim 1 of the formula $$\text{Ado}-\underset{R'_1}{\overset{|}{N}}-\text{CH}-\underset{(CH_2)_mNHR'_5}{\overset{|}{(CH_2)_n}}-\text{NH}_2$$

wherein:
Ado represents 5'-deoxyadenosin-5'-yl;
$R_1'$ represents hydrogen or methyl;
$R_5'$ represents hydrogen or —$(CH_2)_pNH_2$;
n represents an integer of 1 to 4;
m represents an integer of 3 to 7; and
p represents an integer of 2 to 4; or a pharmaceutically acceptable acid addition salt thereof.

8. A compound as claimed in claim 7 wherein n represents 2.

9. A compound as claimed in claim 7 wherein m represents 5.

10. A compound as claimed in claim 7 wherein $R_5'$ represents hydrogen.

11. A compound as claimed in claim 7 wherein $R_5'$ represents —$(CH_2)_3NH_2$.

12. A compound as claimed in claim 7 wherein $R_1'$ represents hydrogen.

13. A compound as claimed in claim 7 wherein $R_1'$ represents hydrogen or methyl, n represents 2, m represents 5 and $R_5'$ represents hydrogen.

14. A compound as claimed in claim 7 wherein $R_1'$ represents hydrogen or methyl, n represents 2, m represents 5 and $R_5'$ represents —$(CH_2)_3NH_2$.

15. A pharmaceutical composition for controlling undesirable cell proliferation in a warm-blooded animal in need thereof comprising a therapeutically effective amount of a compound as claimed in claim 1 as an active ingredient and a pharmaceutically acceptable diluent or carrier.

16. A pharmaceutical composition as claimed in claim 15 in unit dosage form containing 1 to 100 mg of said compound per unit dose.

* * * * *